United States Patent
Keppel

(10) Patent No.: US 6,203,541 B1
(45) Date of Patent: Mar. 20, 2001

(54) AUTOMATIC ACTIVATION OF ELECTROSURGICAL GENERATOR BIPOLAR OUTPUT

(75) Inventor: David Keppel, Longmont, CO (US)

(73) Assignee: Sherwood Services AG, Schaffhausen (CH)

( * ) Notice: Subject to any disclaimer, the term of this patent is extended or adjusted under 35 U.S.C. 154(b) by 0 days.

(21) Appl. No.: 09/298,762

(22) Filed: Apr. 23, 1999

(51) Int. Cl.$^7$ .................................................. A61B 18/12
(52) U.S. Cl. ................................ 606/38; 606/39; 606/40
(58) Field of Search ................................. 606/34, 38, 39, 606/40, 50, 51

(56) References Cited

U.S. PATENT DOCUMENTS

| | | |
|---|---|---|
| 3,964,487 | 6/1976 | Judson . |
| 3,980,085 | 9/1976 | Ikuno . |
| 4,092,986 | 6/1978 | Schneiderman . |
| 4,094,320 | 6/1978 | Newton et al. . |
| 4,188,927 | 2/1980 | Harris . |
| 4,321,926 | 3/1982 | Roge . |
| 4,372,315 | 2/1983 | Shapiro et al. . |
| 4,416,277 | 11/1983 | Newton et al. . |
| 5,514,129 | 5/1996 | Smith . |
| 5,713,896 | * 2/1998 | Nardella ................................. 606/50 |
| 5,827,271 | * 10/1998 | Buysee et al. .......................... 606/40 |
| 5,846,236 | 12/1998 | Lindernmeier et al. . |

FOREIGN PATENT DOCUMENTS

| | | | |
|---|---|---|---|
| 2540968 | * 3/1977 | (DE) | ...................................... 606/40 |
| 9509577 | 4/1995 | (EP) . | |
| 2502935 | * 10/1982 | (FR) | ...................................... 606/40 |
| 727201 | * 4/1980 | (SU) | ...................................... 606/40 |

* cited by examiner

Primary Examiner—Lee Cohen

(57) ABSTRACT

An automatic circuit that controls a surgical instrument having a pair of bipolar electrodes. The circuit comprises means for measuring the current between the pair of electrodes, an impedance detection circuit in electrical communication with the current measuring means, a comparator in electrical communication with the impedance detection circuit and a controller electrically connected to the comparator. The impedance detection circuit calculates the impedance between the electrodes based on the measured current and generates a first signal indicative of the calculated impedance. The comparator processes the first signal and generates an activation signal if the calculated impedance falls within a predetermined range of impedance values and generates a deactivation signal if the calculated impedance exceeds a deactivation threshold. The controller receives the activation and deactivation signals and transmits a first control signal to a radiofrequency energy output stage to activate the electrodes in response to the activation signal and transmits a second control signal to the radiofrequency output stage to deactivate the electrodes in response to the deactivation signal.

14 Claims, 3 Drawing Sheets

AUTOMATIC ACTIVATION OF ELECTROSURGICAL GENERATOR BIPOLAR OUTPUT

BACKGROUND

1. Field of the Disclosure

This application relates to a system for activating and deactivating bipolar electrodes and more particularly relates to a circuit for automatically activating and deactivating an electrosurgical generator based on tissue impedance.

2. Background of Related Art

Electrosurgery is the application of high frequency electrical current to a surgical site for tissue cutting and/or coagulation. In monopolar electrosurgery, a source or active electrode delivers radio frequency energy from the electrosurgical generator to the tissue and a return electrode carries the current back to the generator. In monopolar electrosurgery, the source electrode is typically part of the surgical instrument held by the surgeon and applied to the tissue to be treated. A patient return electrode is placed remote from the active electrode to carry the current back to the generator.

In bipolar electrosurgery, one of the electrodes of the hand-held instrument functions as the active electrode and the other as the return electrode. The return electrode is placed in close proximity to the active (current supplying) electrode such that an electrical circuit is formed between the two electrodes. In this manner, the applied electrical current is limited to the body tissue positioned between the electrodes. When the electrodes are sufficiently separated from one another, the electrical circuit is open and thus inadvertent contact of body tissue with either of the separated electrodes does not cause current to flow. The advantages of bipolar electrosurgery over monopolar electrosurgery include 1) use of lower power level which translates to less tissue destruction, 2) reduced danger of alternate site burns since the only tissue destroyed is that located between the bipolar electrodes; and 3) lower applied voltage which decreases the chance of tissue charring and scarring due to sparks at the electrodes.

Typically, the surgeon activates the electrosurgical generator by a hand or a foot switch to apply current to the body tissue. Such manual operation can cause the surgeon to inadvertently move the bipolar instrument from the desired surgical site as the surgeon activates the switch. Sometimes, to avoid excessive and unwanted surgeon body movement and consequent displacement of the instrument, the surgeon will rely on nurses or other operating room personnel to activate and deactivate the generator. This can cause unintended power delivery or undesired duration of power delivery if not properly coordinated with the surgeon. Also, due to the limits of human reaction time or machine response time when hand or foot activated switches are utilized, repeated desiccation of tissue at consistent levels can sometimes be difficult.

In U.S. Pat. No. 5,514,129, an attempt is made to automatically key the generator to avoid the drawbacks sometimes associated with and hand and foot switches. This keying and control are based on tissue impedance measurements. If the tissue impedance lies within a preset range, the generator is turned on and if the impedance falls below a preset level or exceeds a preset level, the generator is turned off. Patient tissue impedance is measured between the bipolar electrodes by measuring the instantaneous voltage variation and the instantaneous current variation between the electrodes. A first calculator divides the voltage and current proportional signals to generate a signal representative of short circuit impedances. A second calculator divides the voltage and current proportional signals to obtain the changes in impedance between the electrodes. A first comparator compares the signals from the first calculator against a first reference to identify short conditions between the bipolar electrodes and a second comparator compares the signals from the second calculator against a second reference to identify changes in impedance. A logic analyzer electrically connected to the comparators controls the generator by starting, operating and stopping the generator based on the evaluations of the signals from the comparators. The circuit of the '129 patent therefore monitors the voltage and the current and uses those values to calculate the instantaneous impedance, thus requiring the additional steps of repeated calculations to determine the impedance before assessing the impedance ranges. In order to make these measurements of voltage and current variations, RF current must be delivered to the patient.

U.S. Pat. No. 4,416,277 discloses a monopolar system utilizing impedance measurements to mandate termination of power once the generator is already activated and current is being delivered. More specifically, the '277 patent discloses a return electrode monitoring system having patient impedance detection circuitry for producing a voltage which is a function of the impedance between the split electrodes of the return electrode. The voltage signal is applied to adaptive threshold circuitry to determine if the impedance is within a desired range. If the range is exceeded, a signal is generated to disable the generator of the monopolar system.

It would be beneficial to provide a system that automatically activates and deactivates an electrosurgical generator in a bipolar system. The present disclosure provides such a system that utilizes tissue impedance measurements in a bipolar system to not only turn the generator off if the impedance value is exceeded, but to key the generator as well. This automatic activation and deactivation of the generator overcomes the disadvantages associated with manual switches. The circuitry of the present disclosure also simplifies, in part by speeding up the calculations, the activation and deactivation functions.

SUMMARY

The present disclosure provides an automatic circuit that controls a surgical instrument having a pair of bipolar electrodes. The circuit comprises means for measuring the current between the pair of electrodes, an impedance detection circuit in electrical communication with the current measuring means, a comparator in electrical communication with the impedance detection circuit and a controller electrically connected to the comparator. The impedance detection circuit calculates the impedance between the electrodes based on the measured current and generates a first signal indicative of the calculated impedance. The comparator processes the first signal and generates an activation signal if the calculated impedance falls within a predetermined range of impedance values and generates a deactivation signal if the calculated impedance exceeds a deactivation threshold. The controller receives the activation and deactivation signals and transmits a first control signal to a radiofrequency energy output stage to activate the electrodes in response to the activation sigma and transmits a second control signal to the radiofrequency output stage to deactivate the electrodes in response to the deactivation signal. Preferably the first signal is an analog signal and an analog to digital converter receives the first signal and converts it to a digital signal for transmission to the comparator.

The automatic circuit preferably further comprises a filter in electrical communication with the current measuring means for blocking from the impedance detection circuit current from the radiofrequency output stage which would otherwise interfere with the current measuring means.

The current measuring means preferably comprises an oscillator and a transformer for electrically coupling the bipolar electrodes to the oscillator wherein a voltage across a primary winding of the transformer varies in accordance with a variation of impedance between the bipolar electrodes. Preferably the oscillator and transformer are driven at a frequency of about 60 kHz to about 90 kHz. In a preferred embodiment, the activation range of impedance values is from about 20 Ohms to about 500 Ohms and the deactivation threshold is about 2000 Ohms.

The present disclosure also provides an electrosurgical system including a generator for use with bipolar electrodes comprising a current monitor for measuring the current between the bipolar electrodes, an impedance detection circuit in electrical communication with the current monitor to calculate the impedance between the electrodes based on the measured current, a comparator for comparing the calculated impedance to an activation range of impedance values, and a controller for automatically activating the generator if the calculated impedance falls within the activation range of impedance values and deactivating the generator if the calculated impedance exceeds a deactivation threshold.

The system may further include a filter in electrical communication with the current monitor for blocking energy from the bipolar output from the impedance detection circuit.

The system also preferably comprises a transformer in electrical communication with the impedance detection circuit wherein the transformer is driven at a constant voltage and the voltage of a primary winding of the transformer varies in accordance with a variation of the impedance between the electrodes. The transformer transmits a voltage signal proportional to the tissue impedance between the electrodes.

The comparator and the controller preferably form part of a microprocessor and the microprocessor receives and processes the digital impedance signal and generates a digital control signal for activating and deactivating the generator.

A method of automatically activating and deactivating a bipolar electrosurgical radiofrequency generator is also provided. The method comprises the steps of measuring the current between a pair of bipolar electrodes electrically connected to the generator, calculating the impedance between the bipolar electrodes based on the measured current, comparing the calculated impedance to an activation range of impedances, automatically activating the generator if the calculated impedance falls within the activation range, and automatically deactivating the generator if the calculated impedance falls above a deactivation threshold.

The step of calculating the impedance preferably includes the step of driving a transformer at a constant voltage and determining the voltage across a primary winding of the transformer. The method may further include the step of filtering the radiofrequency output current to prevent corruption of the impedance calculation.

BRIEF DESCRIPTION OF THE DRAWINGS

Preferred embodiments of the present disclosure are described herein with reference to the drawings wherein.

DETAILED DESCRIPTION OF THE PREFERRED EMBODIMENTS

Figure 1:
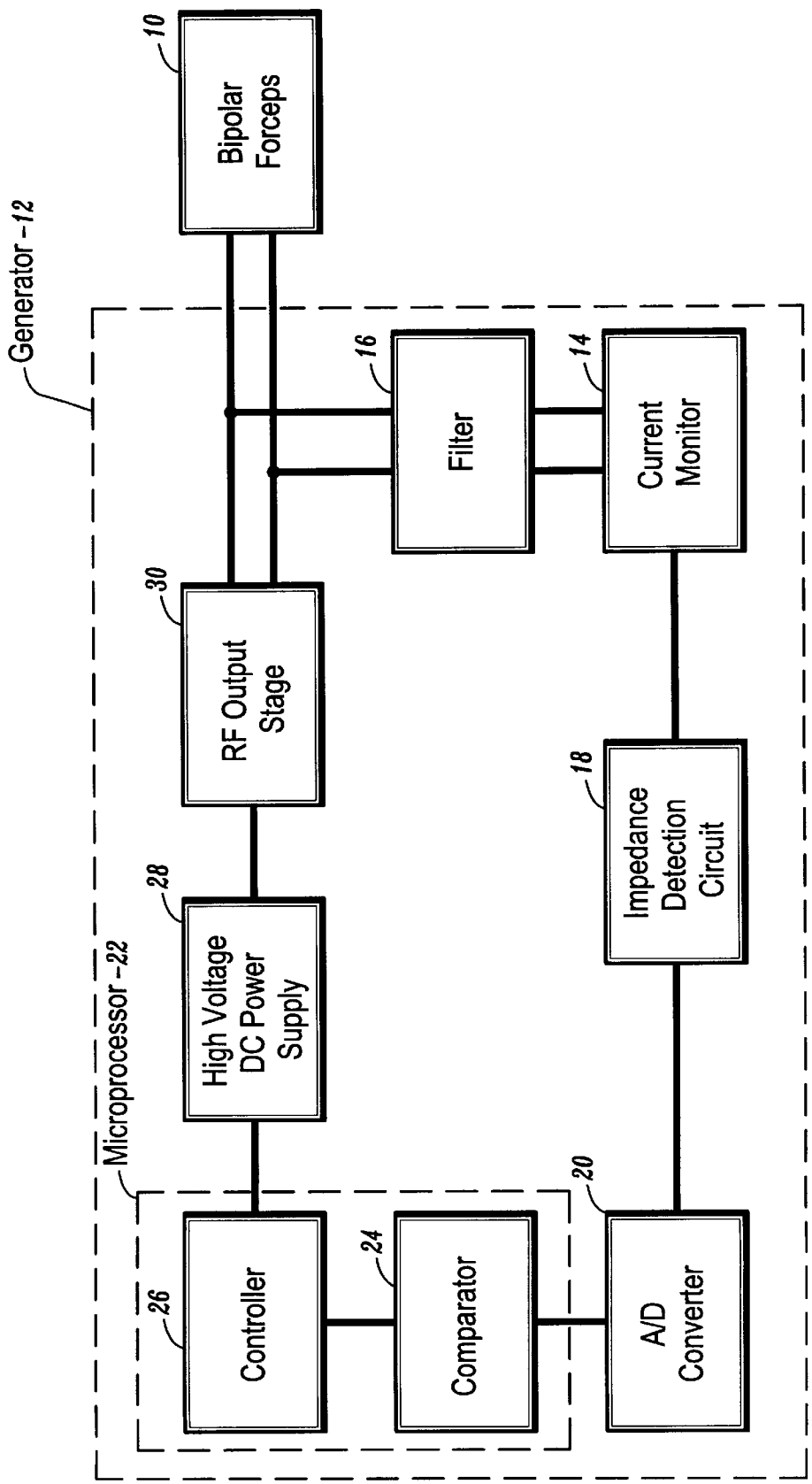
FIG. 1 is a schematic block diagram illustrating the automatic circuit of the present disclosure.

FIG. 1 is a schematic diagram of the bipolar electrosurgical system of the present disclosure. The surgical instrument for treating tissue at the surgical site is designated by reference numeral 10. The instrument 10 is a bipolar instrument typically having a pair of jaws (not shown) which are movable relative to each other to clamp tissue therebetween. A pair of handles (not shown) are activated to move either one or both of the jaws from an open spaced apart position to a closed position. As is conventional in bipolar instruments, one jaw functions as the active electrode to deliver electrical energy from the generator 12 to the tissue to be treated and the other jaw functions as the return electrode to carry the current back to generator 12. In this manner, tissue clamped between the jaws can be cut and/or coagulated by the transmission of electrical energy between the jaws and stray currents are minimized since there is no need for a remote return electrode pad as required in monopolar surgery.

The electrosurgical generator 12 includes a current monitor 14 and an impedance detection circuit 18 electrically connected to the monitor. The current monitor 14 measures the current between the bipolar electrodes of forceps 10 and transmits an analog signal to impedance detection circuit 18 representative of the measured current. The impedance detection circuit 18 calculates the impedance between the bipolar forceps 10 based on the current measurement in the manner described below. An analog to digital converter 20 receives the analog impedance signal from the impedance detection circuit 18, which is indicative of the impedance, and converts it to a digital signal for transmission to the microprocessor 22. The microprocessor 22 preferably includes a comparator 24 and a controller 26, and an output port of the microprocessor 22 is electrically connected to a high voltage DC power supply 28. The comparator 24 evaluates the digital impedance signal by comparing it to predetermined impedance values and generates responsive signals for transmission to the controller 26 as described in detail below. In response to the signals received from the comparator 24, the controller 26 will generate and transmit control signals to the power supply 28 which in turn will control the energy output of the RF output stage 30 which delivers current to the bipolar forceps 10. Filter 16, electrically connected to current monitor 14, blocks energy from RF output stage 30 from entering the impedance detection circuit 18 to effectively eliminate any effect the output current might otherwise have on the impedance calculation.

Figure 2:
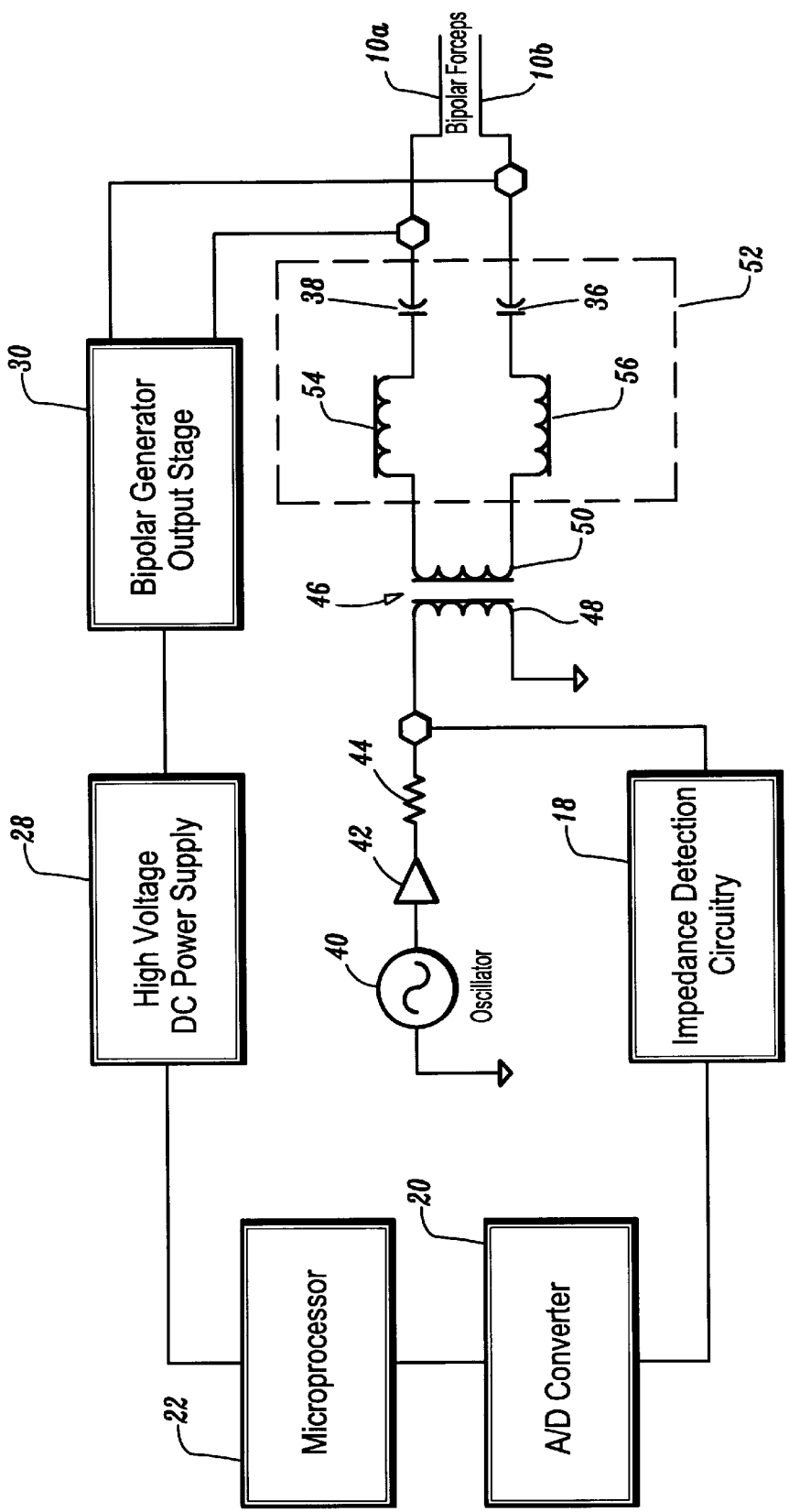
FIG. 2 is a schematic diagram illustrating the automatic circuit for activating and deactivating the generator in response to tissue impedance calculations.

More details of the automatic circuit of the present disclosure will now be described in conjunction with FIG. 2. As shown, jaws (electrodes) 10a and 10b are electrically connected to the RF bipolar output stage 30 so that radiofrequency energy can be supplied to one of the electrodes and returned by the other electrode. Bipolar forceps 10a and 10b are configured for relative movement to clamp tissue therebetween.

The current between the electrodes 10a and 10b is monitored by the provision of an oscillator 40 and an amplifier 42, connected to the output of the oscillator 40, which drive the transformer 46 at a constant voltage. Preferably the transformer 46 is driven at a frequency of about 80KHz, although other frequencies are also contemplated. Current passes through resistor 44 and then through the primary winding 48 of transformer 46.

As the impedance of the tissue changes the current changes inversely proportionally if the voltage remains constant. This is basically defined by Ohm's law where V=RI, wherein V is the voltage across the electrodes in volts, I is the current through the electrodes (and tissue) in milliamps and R is the resistance or impedance of the tissue measured in Ohms. By this equation it can be readily appreciated that when the tissue impedance increases, the current will decrease and conversely, if the tissue impedance decreases, the current will increase. The impedance detection circuit 18 of the present disclosure essentially measures impedance based on the changes in current. Initially, when the tissue impedance is relatively low, this means the forceps have not fully clamped the tissue. Once properly clamped, since the tissue prior to electrosurgical treatment is more conductive, when energy is applied, the impedance will be low. As the tissue is treated and dessicates, the conductivity decreases as the tissue moisture content decreases. Consequently tissue impedance will increase.

More specifically, the oscillator 40 and amplifier 42 deliver a monitoring current to the bipolar forceps 10. The primary winding 48 of transformer 42 is in circuit with the output of the oscillator 40 and the secondary winding 50 is connected to forceps 10a and 10b. Current delivered from oscillator 40 passes through resistor 44 as shown. As the tissue impedance changes, the impedance reflected to the primary side 48 of the transformer 40 will accordingly vary as the variation on the primary side depends on the impedance variation of the secondary side of 50 of the transformer 46. Thus by processing the voltage at the primary side 48, which will change proportionally to the impedance change, impedance can be determined. The impedance detection circuit 18 processes the voltage appearing across the forceps 10a, 10b and generates an analog signal representative of the impedance measurement. As mentioned above, this analog signal is converted to a digital signal for processing by microprocessor 22.

The automatic circuit also includes a band pass filter 52 which functions to substantially eliminate any effect the electrosurgical generator 12 might have on the production of the analog impedance signal when the generator 12 has been activated. That is, the band pass filter 52 in effect blocks form the transformer 46 any output current from the bipolar RF stage 30 output which would otherwise distort the current measurement and consequently, the impedance calculation. As shown in FIG. 2, current passes through capacitors 36 and 38, connected in parallel, and coils 54, 56 of filter 52.

In a preferred embodiment, a second filter (not shown) is provided to shunt energy to ground which undesirably passes through the band pass filter 52 as a further protection against signal distortion. This additional filter could be part of the impedance detection circuit 18 or separate therefrom.

Figure 3:
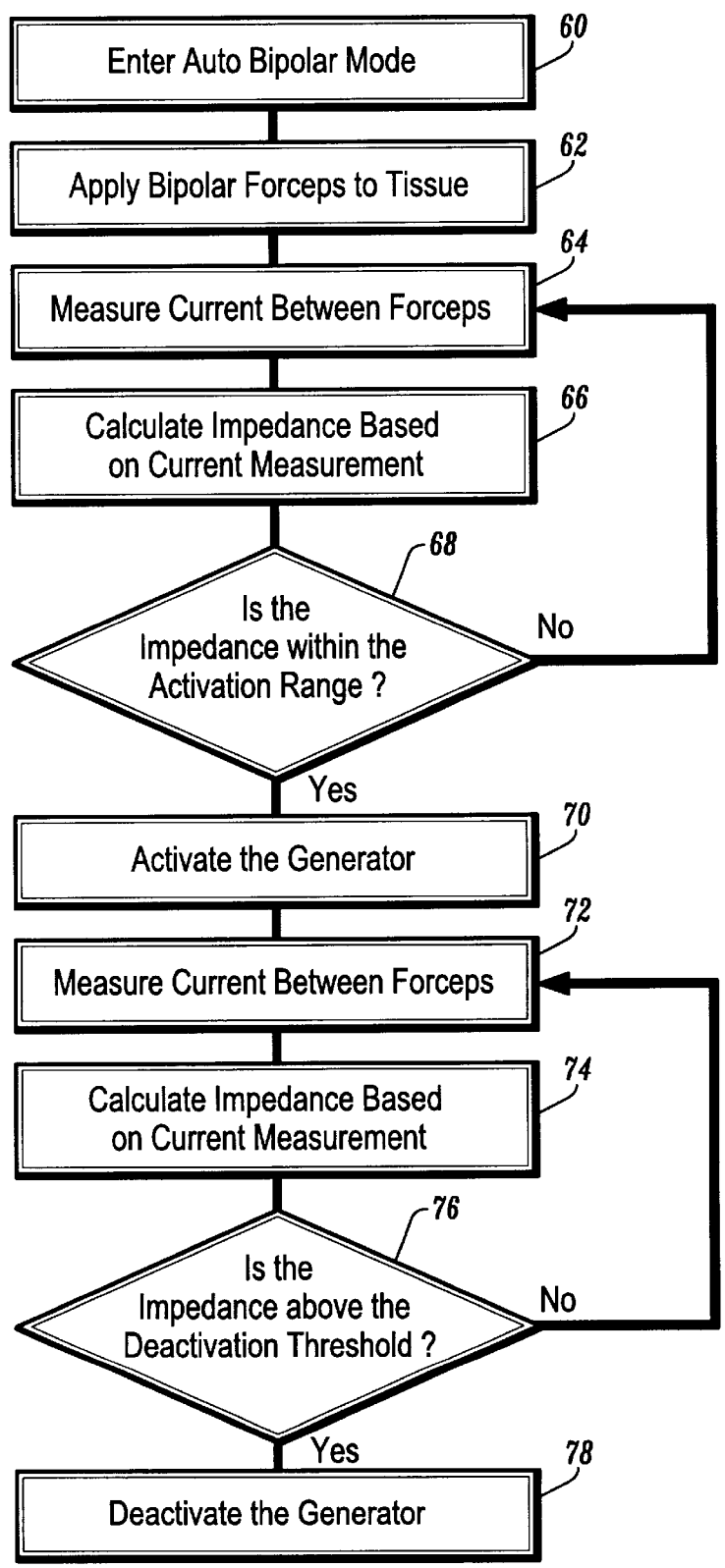
FIG. 3 is a flow diagram showing the steps followed for determining automatic activation and deactivation of the electrosurgical generator.

In conjunction with the flow diagram of FIG. 3 and the schematic and circuit diagrams of FIGS. 2 and 3, the steps followed for automatically activating and deactivating the electrosurgical generator 12 will now be described. In the first step, (block 60) the automatic bipolar mode is entered by activating the oscillator 40 to deliver monitoring current to the forceps 10 which are applied to the tissue in step 62. The current between the forceps (electrodes) 10a, 10b is measured in the manner described above as the voltage across the forceps varies in accordance with impedance variation. Next, the impedance between the forceps 10a, 10b is calculated based on the current measurement by the impedance detection circuitry and an analog impedance signal is transmitted to an analog to digital converter 20 (FIGS. 1 and 2). The digital impedance signal generated by the A/D converter is transmitted to the comparator 24 of the microprocessor 22 where it is compared to a preset activation range of impedances. As represented by block 68, if the impedance does not fall within the activation range, e.g., the impedance is too low, then the electrodes 10a, 10b have not fully clamped the tissue as necessary and the generator will not be automatically activated. However, the monitoring current will continue to be applied and the current will continue to be measured in accordance with step 64. Note that the monitoring current is continuously delivered by the oscillator 40 throughout the procedure.

If the impedance does fall within the activation range (step 68) then the generator 12 is automatically activated as represented by step 70. Thus, the activation range of impedances is preset to correspond to the condition when the forceps have sufficiently clamped tissue such that radiofrequency energy should be applied to treat the tissue. In a preferred embodiment, the activation range of impedances is from about 20 Ohms to about 500 Ohms. Activation of the generator 12 occurs as the comparator 24 transmits a digital activation signal to the controller 26. The controller 26 transmits a digital control signal to the DC power supply 28 in response to the activation signal which in turn enables the RF output stage 30 to deliver current to the forceps 10 to treat e.g. cut and/or coagulate, tissue.

Once the generator is automatically activated, the current measurement between the forceps continues to be calculated in the identical manner as in step 64. The impedance is subsequently calculated, represented by step 74, by the impedance detection circuit 18 as described above and in an identical manner as step 68. It should be appreciated that step 64 is identical to step 72 and step 66 is identical to step 74, but are set forth as separate blocks for the purpose of clarity.

Since the generator has been activated, the impedance calculation is also compared to a preset deactivation threshold by the comparator 24. It should be appreciated that this step 76 occurs only if the generator has been activated by an affirmative response to step 68; if the impedance is outside the range of step 68, the loop of steps 64–68 continues until such time that the generator is automatically activated.

The deactivation threshold value is preferably about 2000 Ohms. If the impedance calculation exceeds this deactivation threshold, this indicates that the tissue has been treated since the impedance increases as the tissue is desicated because its conductivity due to moisture loss has decreased. If the deactivation threshold is exceeded, a digital deactivation signal is transmitted from the comparator 24 to the controller 26. The controller 26 receives this deactivation signal and transmits a control signal to the power supply 28 to automatically deactivate the generator so current delivery from RF output stage 30 is terminated, thereby preventing overheating and unwanted destruction of tissue.

As can be appreciated, the present disclosure advantageously provides a method of automatically activating and deactivating on electrosurgical radiofrequency generator based on impedance measurements. The impedance measurements are calculated based on the measured current between the bipolar forceps and the impedance values are compared to preset impedance values. The ranges provided herein are by way of example, as other ranges and activation/deactivation thresholds can be utilized. The automatic circuit disclosed herein can be used, by way of example, with Valleylab's current Ligasure* instruments which apply RF energy to seal vessels. However, use with other instruments is also contemplated.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. An automatic circuit that controls a surgical instrument having a pair of bipolar electrodes, the circuit comprising:
    means for measuring the current between the pair of electrodes, said measuring means including;
        means for generating a constant voltage;
        a transformer having a primary winding and a secondary winding, said primary winding having a signal end for receiving a signal and a return end, said secondary winding coupled to the pair of electrodes; and
        a resistive element in series with said generating means and said signal end, wherein a voltage developed across said signal end and said return end of said primary winding is representative of a measured current between the pair of bipolar electrodes;
    an impedance detection circuit in electrical communication with said measuring means for calculating the impedance based on the measured current, the impedance detection circuit generating a first signal indicative of the calculated impedance;
    a comparator in electrical communication with the impedance detection circuit, the comparator processing the first signal and generating an activation signal if the calculated impedance falls within a predetermined range of impedance values and generating a deactivation signal if the calculated impedance exceeds a deactivation threshold; and
    a controller in electrical communication with the comparator for receiving the activation and deactivation signals and transmitting a first control signal to a radiofrequency energy output stage to activate the electrodes in response to the activation signal and transmitting a second control signal to the radiofrequency output stage to deactivate the electrodes in response to the deactivation signal.

2. The circuit of claim 1, further comprising a filter in electrical communication with said measuring means for blocking from the impedance detection circuit current from the radiofrequency output stage that would otherwise interfere with the current measuring means.

3. The circuit of claim 2, wherein the first signal is an analog signal, and wherein the automatic circuit further comprises an analog to digital converter for receiving the first signal and converting it to a digital signal that is transmitted to the comparator.

4. The circuit of claim 1, wherein said measuring means includes an oscillator, and wherein the oscillator and the transformer are driven at a frequency of about 60 kHz to about 90 kHz.

5. The circuit of claim 1, wherein the predetermined range of impedance values is from about 20 Ohms to about 500 Ohms.

6. The circuit of claim 5, wherein the deactivation threshold is about 2000 Ohms.

7. An electrosurgical system including a generator for use with bipolar electrodes comprising:
    a current monitor for measuring the current between the bipolar electrodes including a transformer having a primary winding with a first end driven at a constant voltage through a resistive element and a second end coupled to a return, wherein the voltage across the primary winding of the transformer varies in accordance with a variation of a current between the electrodes;
    an impedance detection circuit in electrical communication with the current monitor to calculate the impedance between the electrodes based on the measured current;
    a comparator for comparing the calculated impedance to an activation range of impedance values; and
    a controller for automatically activating the generator if the calculated impedance falls within the activation range of impedance values and deactivating the generator if the calculated impedance exceeds a deactivation threshold.

8. The system of claim 7, further comprising a filter for blocking energy from an output of the generator from the impedance detection circuit, the filter being in electrical communication with the current monitor.

9. The system of claim 7, further comprising an analog to digital converter in electrical communication with the impedance detection circuit for converting an analog impedance signal from the impedance detection circuit to a digital impedance signal.

10. The system claim 9, wherein the comparator and the controller form part of a microprocessor, and wherein the microprocessor receives and processes the digital impedance signal and generates a digital control signal for activating and deactivating the generator.

11. The system of claim 7, wherein the activation range of impedance values is from about 20 Ohms to about 500 Ohms.

12. The system of claim 11, wherein the deactivation threshold is about 2000 Ohms.

13. A method of automatically activating and deactivating a bipolar electrosurgical radiofrequency generator comprising the steps of:
    measuring the current between a pair of bipolar electrodes electrically connected to the generator utilizing a transformer driven at a constant voltage through a resistive element and determining the voltage across a primary winding of the transformer;
    calculating the impedance between the bipolar electrodes based on the measured current;
    comparing the calculated impedance to an activation range of impedances;
    automatically activating the generator if the calculated impedance falls within the activation range; and
    automatically deactivating the generator if the calculated impedance falls above a deactivation threshold.

14. The method of claim 13, further comprising the step of filtering a radiofrequency output current of the generator to prevent corruption of the impedance calculation by said radiofrequency output.

* * * * *